(12) United States Patent
Jones (10) Patent No.: US 9,162,045 B2
(45) Date of Patent: Oct. 20, 2015

(54) BIOMEDICAL ELECTRODE (75) Inventor: Deborah T. Jones, Dartmouth, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 403 days.

(21) Appl. No.: 13/079,336

(22) Filed: Apr. 4, 2011

(65) Prior Publication Data

US 2012/0253162 A1 Oct. 4, 2012

(51) Int. Cl.
*A61N 1/05* (2006.01)
*A61B 5/0408* (2006.01)
*A61N 1/04* (2006.01)

(52) U.S. Cl.
CPC ............... *A61N 1/046* (2013.01); *A61N 1/0472* (2013.01); *A61N 1/0488* (2013.01); *A61N 1/0492* (2013.01); *A61B 2562/125* (2013.01)

(58) Field of Classification Search
CPC ... A61N 1/0492; A61N 1/048; A61N 1/0472; A61N 1/046; A61N 1/0488; A61N 1/0496; A61B 5/04087; A61B 2562/125
USPC .................. 600/382, 391, 392; 607/142, 149
See application file for complete search history.

(56) References Cited

U.S. PATENT DOCUMENTS

| 4,243,051 A | 1/1981 | Wittemann |
| 5,356,428 A | 10/1994 | Way |
| 5,571,165 A | 11/1996 | Ferrari |
| 5,733,324 A | 3/1998 | Ferrari |
| 5,824,033 A | 10/1998 | Ferrari |
| 5,916,244 A * | 6/1999 | Walters .......................... 607/142 |
| 6,600,957 B2 | 7/2003 | Gadsby |
| 7,069,074 B2 * | 6/2006 | Covey et al. ....................... 607/5 |
| 7,169,644 B2 | 1/2007 | Ferrari |
| 7,187,985 B2 | 3/2007 | Carim |
| 7,392,096 B2 | 6/2008 | Ferrari |
| 7,822,488 B2 | 10/2010 | Jonsen et al. |
| 2005/0015134 A1 | 1/2005 | Carim |
| 2006/0178706 A1 | 8/2006 | Lisogurski et al. |
| 2010/0152827 A1 | 6/2010 | Wilfinger |

FOREIGN PATENT DOCUMENTS

EP          1905479 A1    4/2008

OTHER PUBLICATIONS

Notification of Transmittal of the International Search Report and Written Opinion of the International Searching Authority from corresponding PCT/US2012/032011 dated Feb. 19, 2013.

* cited by examiner

Primary Examiner — Tammie K Heller
(74) Attorney, Agent, or Firm — Lando & Anastasi, LLP (57) ABSTRACT An electrode and electrodes for a biomedical system is provided. The electrode includes a backing pad with top and bottom surfaces. A conductive element is attached to the bottom surface of the backing pad, and a conductive gel layer covers at least part of the bottom surface of the conductive element. A bonding layer is disposed at least in part between the conductive element and the conductive gel layer. The electrode can include a leadwire with a stripped end length, and at least a portion of the stripped end length is disposed between the conductive element and at least one of the bonding layer and the conductive gel layer.

23 Claims, 9 Drawing Sheets

BIOMEDICAL ELECTRODE

BACKGROUND OF THE INVENTION

1. Field of Invention

At least one embodiment of the present invention relates generally to a biomedical electrode, and more specifically, to a transcutaneous electrode configured to apply therapy to a subject.

2. Discussion of Related Art

Cardiac arrest and other health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. Health care professionals also attempt to detect and prevent conditions conducive to cardiac ailments by examining and treating patients. These efforts are expensive and have a limited success rate, and cardiac arrest, among other conditions, continues to claim the lives of victims.

SUMMARY OF THE INVENTION

Aspects and embodiments of the present invention are directed to a multifunction biomedical electrode, and systems and methods of its use and manufacture. At least one electrode can adhere to a subject to apply treatment in the form of an electric shock, for example to defibrillate or pace the subject. The electrode can also pass electrical energy to the subject to stimulate a portion of the subject's body, and can monitor the condition of the subject. The multifunction electrode can be radiolucent, or substantially X-Ray transmissive so that an X-Ray image of a subject that is sufficient for medical diagnosis may be ascertained with the electrode adhered to the subject.

At least one aspect is directed to an electrode including a backing pad having a top surface and a bottom surface. The electrode also includes a conductive element attached to the bottom surface of the backing pad, and a conductive gel layer covering at least part of a bottom surface of the conductive element. The electrode includes a bonding layer disposed at least in part between the conductive element and the conductive gel layer. The electrode also includes a leadwire having a stripped end length. At least a portion of the stripped end length is disposed between the conductive element and at least one of the bonding layer and the conductive gel layer. In some embodiments, the portion of the stripped end length of the leadwire is disposed proximate to a bottom surface of the conductive element.

In some embodiments, the electrode includes an insulator disposed at least in part between at least a portion of the conductive gel layer and the portion of the stripped end length of the leadwire. A bottom surface of the insulator and a bottom surface of the backing pad may include adhesive, and the surface area of the bottom surface of the insulator can be less than half of a surface area of the bottom surface of the backing pad. In one embodiment, the bonding layer is disposed at least in part between the insulator and the portion of the stripped end length of the leadwire.

In some embodiments, the electrode includes a hotmelt adhesive disposed on the leadwire. The electrode can also include a label on the top surface of the backing pad with instructions associated with the electrode. In one embodiment, the electrode includes a tab extending from the backing pad, and a surface of the tab can be free of adhesive. The leadwire can include a conductive carbon element, and the stripped end length can include a plurality of stripped extensions. In some embodiments, the plurality of stripped extensions is in a fanned configuration, and at least one of the plurality of stripped extensions has a round cross section.

In one embodiment, the electrode is radiolucent. The electrode can include at least one of a therapy electrode, a treatment electrode, a stimulating electrode, and a monitoring electrode. The electrode can be configured to adhere to a subject.

At least one aspect is directed to a biomedical electrode system. The system includes a first electrode configured to adhere to a first location of a subject, and a second electrode configured to adhere to a second location of the subject. The first electrode includes a backing pad having a top surface and a bottom surface, and a conductive element attached to the bottom surface of the backing pad. The first electrode also includes a conductive gel layer covering at least part of a bottom surface of the conductive element and a bonding layer disposed at least in part between the conductive element and the conductive gel layer. The first electrode also includes a leadwire having a stripped end length. At least a portion of the stripped end length is disposed between the conductive element and at least one of the bonding layer and the conductive gel layer.

In some embodiments, the first electrode is an anterior electrode configured for placement proximate to a chest of a subject, and the second electrode is a posterior electrode configured for placement proximate to a back of the subject. In one embodiment, the first electrode and second electrodes are anterior electrodes configured for placement proximate to a chest of a subject. In one embodiment, the first electrode and the second electrode are configured to form part of a circuit to apply electrical energy to a subject. The anterior electrode can have a substantially circular profile, and the posterior electrode can have a substantially rectangular profile.

In one embodiment, the system includes a connector configured to receive the leadwire of the first electrode and to receive a leadwire of the second electrode. The system can also include a containment element configured to secure the leadwire of the first electrode and the leadwire of the second electrode.

At least one aspect is directed to a method of facilitating care of a subject. The method includes an act of providing an electrode. The electrode includes a backing pad having a top surface and a bottom surface and a conductive element attached to the bottom surface of the backing pad. The electrode also includes a conductive gel layer covering at least part of a bottom surface of the conductive element, and a bonding layer disposed at least in part between the conductive element and the conductive gel layer. The electrode also includes a leadwire having a stripped end length, with at least a portion of the stripped end length disposed between the conductive element and the conductive gel layer.

In one embodiment, the method includes an act of providing instructions directing a user to position the electrode on the subject. The method can also include an act of providing the electrode, wherein the electrode includes an insulator disposed at least in part between at least a portion of the conductive gel layer and the portion of the stripped end length of the leadwire, and wherein the bonding layer is disposed at least in part between the insulator and the portion of the stripped end length of the leadwire. In some embodiments, the method includes an act of providing the electrode in a package, and an act of providing a second electrode in the package.

In some embodiments, the method includes an act of providing instructions to position the electrode on a first location of the subject. The method can also include an act of providing instructions to position a second electrode on a second location of the subject. In one embodiment, the method includes an act of providing instructions to adhere the electrode to the subject, proximate to a heart of the subject. The method can also include an act of providing instructions to remove the electrode from the subject.

These and other aspects and embodiments are discussed in detail below. The foregoing information and the following detailed description include illustrative examples of various aspects and embodiments, and provide an overview or framework for understanding the nature and character of the claimed aspects and embodiments. The drawings provide illustration and a further understanding of the various aspects and embodiments, and are incorporated in and constitute a part of this specification. The drawings, together with the remainder of the specification, serve to describe and explain the claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including" "comprising" "having" "containing" "involving" and variations thereof herein, is meant to encompass the items listed thereafter, equivalents thereof, and additional items, as well as alternate embodiments consisting of the items listed thereafter exclusively.

Figure 1:
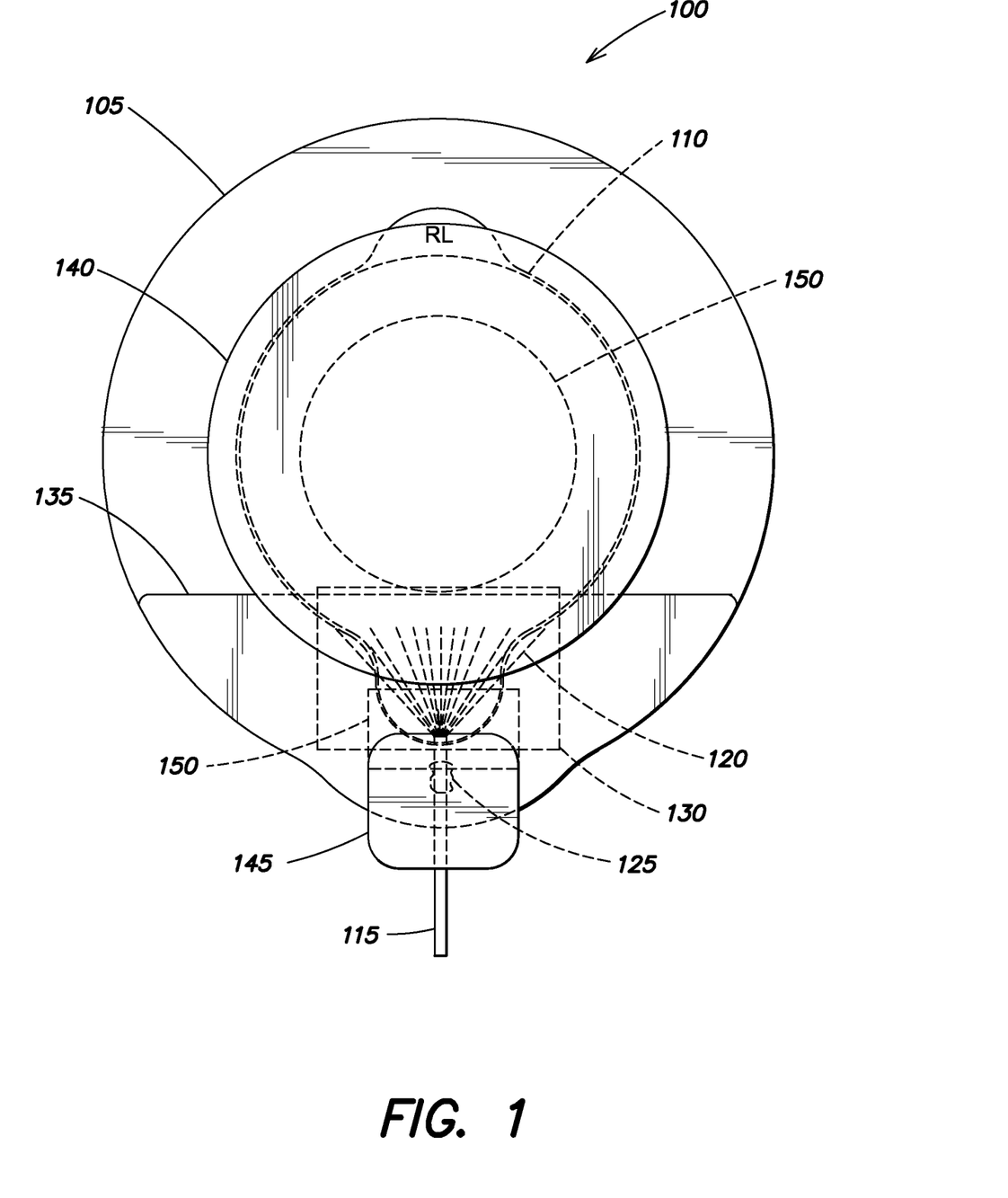
FIG. 1 is a plan view depicting an electrode in accordance with an embodiment.
Figure 2:
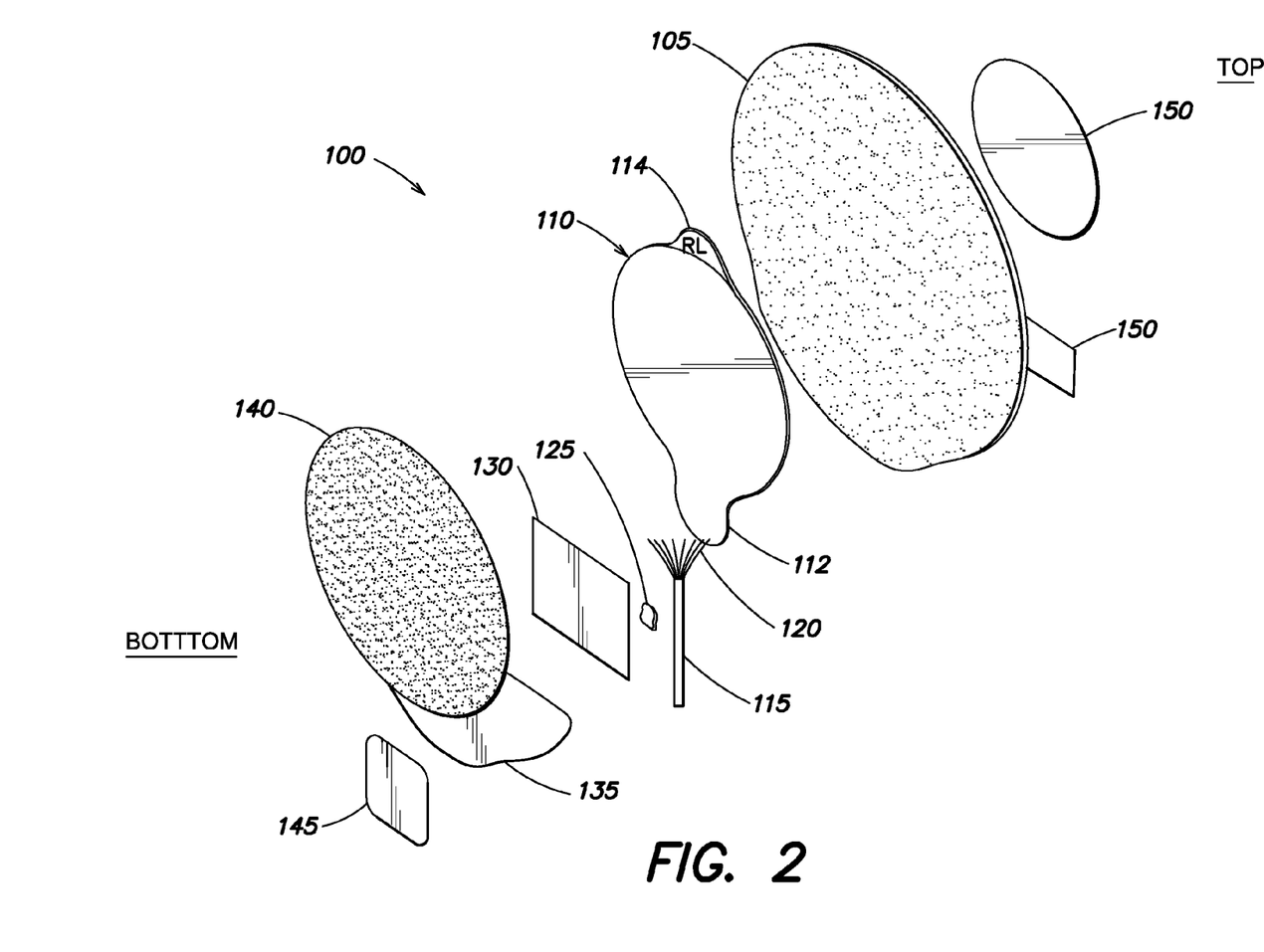
FIG. 2 is an exploded perspective view of the electrode of FIG. 1.
Figure 3:
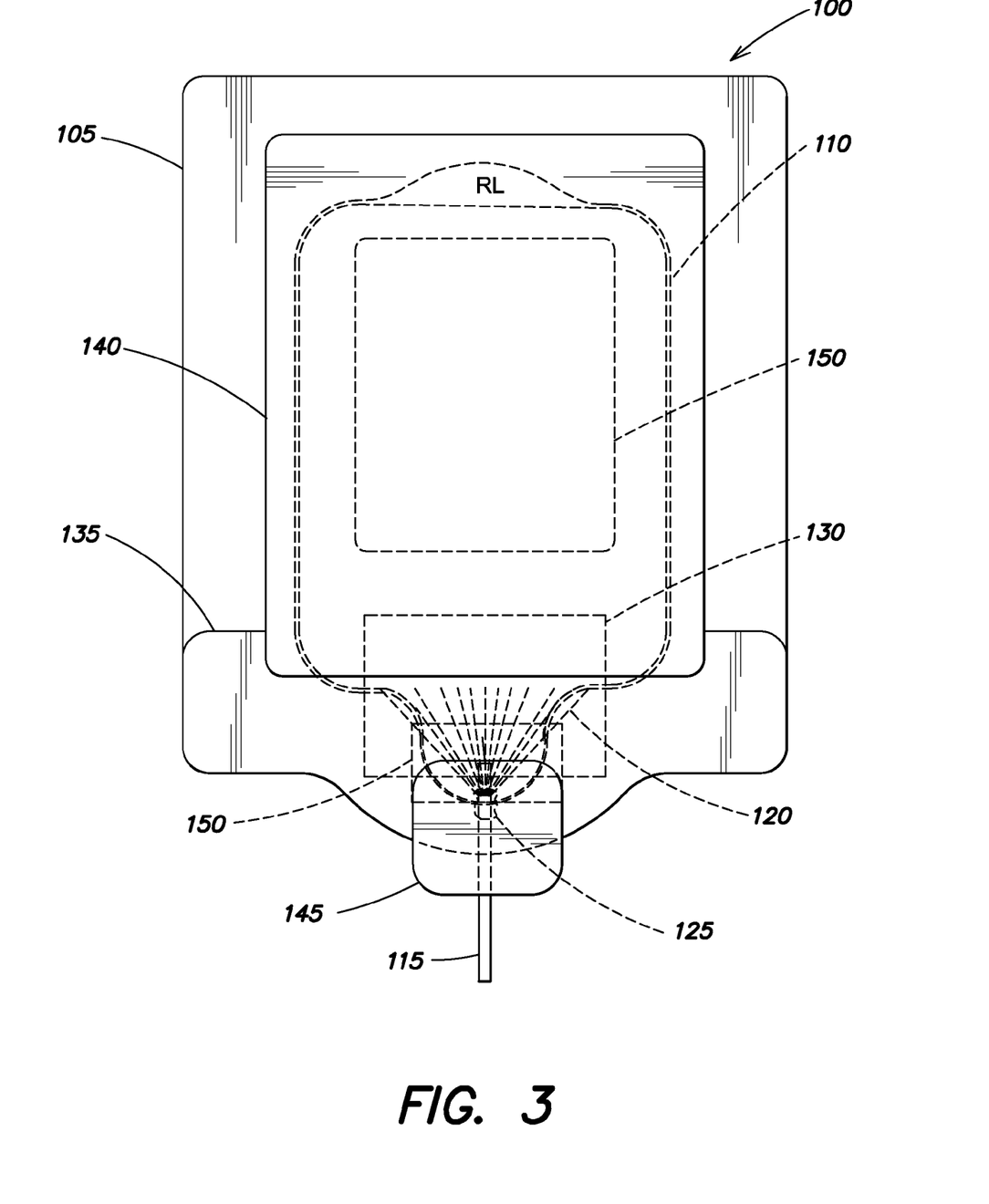
FIG. 3 is a plan view depicting an electrode in accordance with another embodiment.
Figure 4:
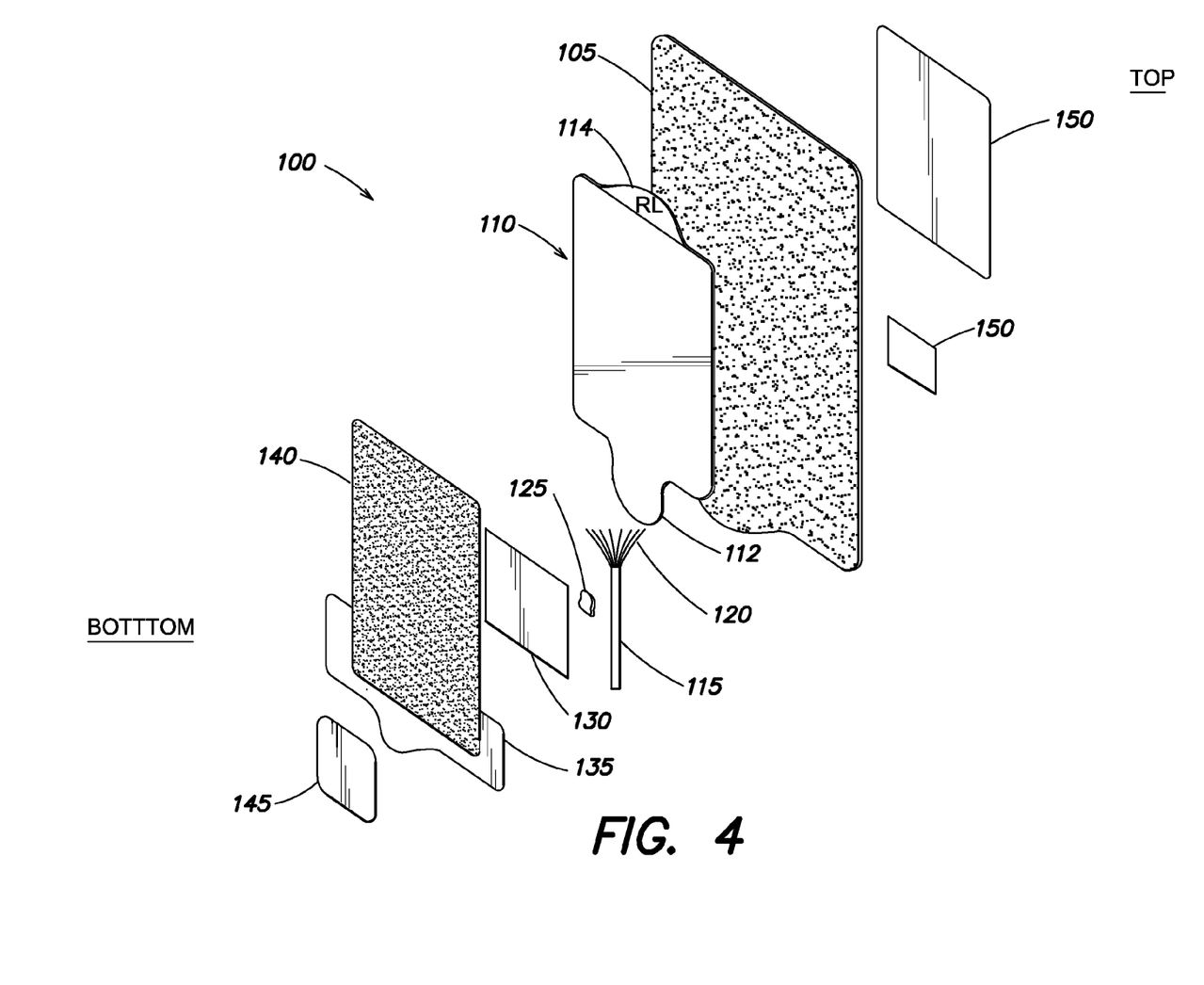
FIG. 4 is an exploded perspective view of the electrode of FIG. 2.

FIG. 1 is a plan view depicting an electrode 100 in accordance with one embodiment, and FIG. 2 is an exploded view of electrode 100 of FIG. 1. FIG. 3 is a plan view depicting an electrode 100 in accordance with another embodiment, and FIG. 4 is an exploded view of the electrode 100 of FIG. 4. In one embodiment, electrode 100 is a multifunction electrode. For example electrode 100 can be a biomedical electrode to administer an electric shock to a subject for defibrillation, pacing, or to stimulate muscle contraction. Electrode 100 can also be a monitoring electrode to monitor or detect, for example, electrical activity of a subject's heart. This information can be used to generate an electrocardiogram. Electrode 100 can be placed proximate to a subject and coupled with power sources and control logic to deliver electrical energy to the subject, to determine the timing, levels, and history of applied energy, and to process monitored or detected data for analysis by a health care provider, for example. Electrode 100 may be located proximate to the subject, e.g., attached, connected, or coupled to the subject, at an anterior, posterior, lateral, or other location of the subject. For example, electrode 100 can be attached to the subject's chest, back, side, head, abdomen, torso, thorax, or legs. In one embodiment, electrode 100 is an external electrode attached to the subject proximate to the subject's heart. Electrodes 100 can be disposable or configured for repeated use.

In one embodiment, when proximate to a subject, the top surface of electrode 100 and its components face away from the subject, and the bottom surface of electrode 100 and its components face toward the subject. FIGS. 2 and 4 identify which surfaces of electrode 100 are considered the top surface and the bottom surface in one embodiment. Some of the bottom surfaces may contact the subject by, for example, adhering to the subject's skin. In one embodiment, electrode 100 is substantially flat. For example, electrode 100 may have a flat profile that is not noticeable or is minimally noticeable when attached to the subject, under the subject's clothes. Electrode 100 may also be substantially flexible. For example, electrode 100 can conform to the contours of the subject's body during initial attachment to the subject, and can conform to body positioning changes when the subject is in motion. Electrode 100 can also be substantially devoid of rigid components, such as hard snaps, connectors, and rigid plates. For example, electrode 100 may be devoid of hard rigid substances that may cause uncomfortable pressure points when a subject with electrode 100 attached to his/her body is in a prone, prostrate, supine, or lateral position with electrode 100 pressed against an object, such as a bed, couch, medical examining table, clothes, or medical equipment. Electrode 100 can be compliant with the American National Standards Institute (ANSI) standards for electrodes, or with the Association for the Advancement of Medical Instrumentation (AAMI) standards for electrodes.

In one embodiment, electrode 100 includes at least one backing pad 105, with a top surface of backing pad 105 configured to face away (e.g., outward) from the subject wearing electrode 100 and a bottom surface of backing pad 105 configured to face toward (e.g., inward) the subject. At least a portion of the bottom surface of backing pad 105 (e.g., a peripheral surface of backing pad 105) can contact the subject, when the subject is wearing electrode 100. In one embodiment, backing pad 105 includes a flexible, stretchable film, such as polyethylene foam that insulates the top (e.g., outer) surface of electrode 100 from electrical current. In one embodiment, backing pad 105 has a thickness of $1/16^{th}$ of an inch, +/−20%. Backing pad 105 can have other thicknesses, both more and less than 1/16$^{th}$ of an inch. Backing pad 105 may include instructions, pictures, identifiers, or warnings. For example, words, symbols, or images can be printed on the top or bottom surfaces of backing pad 105.

In one embodiment, the bottom surface of backing pad 105 includes an adhesive, such as a pressure sensitive adhesive. The adhesive may cover all, substantially all, or part of the bottom surface of backing pad 105 to provide adhesion of electrode 100 to the subject or to other electrode 100 components. The top surface of backing pad 105 may be free of adhesive. In one embodiment, backing pad 105 defines the footprint, or outer boundary or profile of electrode 100. Portions of electrode 100 components (e.g., wires, tabs, labels) may extend beyond this footprint.

Backing pad 105 may have various shapes and sizes that delineate the approximate footprint of electrode 100. For example, backing pad 105 and electrode 100 can be substantially circular, as depicted in FIGS. 1 and 2, among others. A substantially circular backing pad 105 may have a diameter of between 5.5 and 6.5 inches. Backing pad 105 can have other diameters above and below this range, such as between 3 and 4 inches, or between 2 and 3 inches. In one embodiment, a substantially circular backing pad 105 is part of an anterior electrode configured for placement proximate to the subject's chest. In one embodiment, backing pad 105 and electrode 100 are substantially rectangular, as depicted in FIGS. 3 and 4, among others. A substantially rectangular backing pad 105 may have a length of between 6 and 7 inches (e.g., 6.5 inches), and a width of between 4.5 and 5.5 inches (e.g., 5 inches). In some embodiment, backing pad 105 is substantially rectangular with a length of between 4.5 and 5.5 inches and a width between 3 and 4 inches, or a length between 2 and 3 inches and a width between 1.5 and 2.5 inches. Backing pad 105 may also have other dimensions, greater and less than these ranges, as well as larger and smaller length to width ratios.

In one embodiment, electrode 100 includes at least one conductive element 110. Electrical energy can transfer from a power source coupled with electrode 100 to a subject wearing electrode 100 via at least one conductive element 110. For example, conductive element 110 can conduct sufficient electrical current (e.g., up to 60 A for up to 40 ms) over an area sufficiently large to apply defibrillation or pacing therapy to the subject, and with sufficient energy (e.g., 1-370 Joules). In one embodiment, conductive element 110 includes a film covered at least in part with conductive ink. The film that is covered with the conductive ink may be conductive or non-conductive. The conductive ink can be applied to the film via, for example, a screen printing method. In one embodiment, conductive element 110 includes a metal/metal chloride covering, such as silver/silver chloride. Conductive element 110 may be flexible (e.g., a film covered with conductive ink) or rigid (e.g., a metal or other conductive plate). In one embodiment, conductive element 110 includes a non-conductive plate covered at least in part with conductive ink.

In one embodiment, a top surface of conductive element 110, which faces away or outward from a patient wearing electrode 100, is coupled with the bottom surface of backing pad 105. For example, the top surface of conductive element 110 or the bottom surface of backing pad 105 can include an adhesive to couple these two elements together. Conductive element 110 may be substantially circular, for example as depicted in FIGS. 1 and 2. A substantially circular conductive element 110 may have a diameter of substantially 3.5 inches, (e.g., between 3 and 4 inches), or substantially 2 inches (e.g., between 1.5 and 2.5 inches). A substantially circular conductive element can have other diameters greater and less than these ranges. In one embodiment, conductive element 110 is substantially rectangular, for example as depicted in FIGS. 3 and 4. A rectangular conductive element 110 can have a length of substantially 4.5 inches (e.g., 4 to 5 inches) and a width of substantially 3 inches (e.g., 2.5-3.5 inches). In some embodiments, rectangular conductive element 110 has a length of substantially 3.25 inches (e.g., between 2.5 and 3.5 inches) and a width of substantially 1.75 inches (e.g., between 1.5 and 2.5 inches); or a length of substantially 2.0 inches (e.g., between 1.5 and 2.5 inches) and a width of substantially 1.75 inches (e.g., between 1.0 and 2.0 inches).

Conductive element 110 in circular, square, or other configurations may also include at least one protruding tab or extension that extends approximately one inch out from the edges of conductive element 110, (e.g., deviating from the circumference of the circle or parallel line outline of the rectangle). Components of electrode 100 can couple to this protrusion to connect with conductive element 110. In one embodiment, conductive element 110 includes two protrusions, a first protrusion 112 of approximately one inch that may connect with components of electrode 100, and a second protrusion 114 that may be smaller than the first protrusion and that may contain information about electrode 100 or about conductive element 110.

In one embodiment, conductive element 110 is radiolucent, and protrusion 114 may include writing or symbols to indicate, for example, that conductive element 110 is radiolucent, or to identify top or bottom surfaces to assist and verify the assembly or disassembly processes. A radiolucent conductive element 110, for example, includes at least some degree of X-Ray transmissivity, with minimal or generally uniform X-Ray attenuation. Radiolucent conductive element 110 may appear in an X-Ray image, however, the X-Ray image of the portion of the subject's body covered by radiolucent conductive element 110 can be of sufficient quality to allow for a medical diagnosis. Accordingly, the subject can continuously wear electrode 100, including during periods of medical examination, without hindering the examination. Conductive element 110 may also be radiotransparent and may not appear in any X-Ray image.

In one embodiment, electrode 100 includes at least one leadwire 115. For example, one end of leadwire 115 can couple with electrode 100, and another end of leadwire 115 can couple with a power source. In one embodiment, electrode 100 including leadwire 115 form part of a circuit that includes the subject, and electrical current can be applied to the subject wearing electrode 100 from the power source via leadwire 115. The power source may be associated with a defibrillator, pacing unit, or monitor. Information sensed by electrode 100 can also be provided from electrode 100 to a control unit of a defibrillator, pacing unit, or monitor for processing or evaluation. In one embodiment, leadwire 115 has a length of at least 36 inches. The leadwire can also have a length of less than 36 inches.

Leadwire 115 may include a low resistance wire, for example having a resistance of less than 0.2 Ohms/foot, with an insulated coating or jacket. In one embodiment, leadwire 115 includes metal or conductive metal coated carbon fibers. For example, leadwire can include a 12,000 strand nickel plated carbon wire fiber with 4 tinned copper strands. In one embodiment, leadwire 115 includes stripped end length 120. Stripped end length 120 includes an unsheathed portion of leadwire 115 with exposed conductive wires or filaments. Stripped end length 120 may have a length of substantially one inch or less. For example, stripped end length 120 may include a plurality of extensions (e.g., wires, strands, or filaments) extending in a fanned configuration, with each extension having a length of one inch or less. The lengths of the individual extensions can be uniform or they may vary. Stripped end length 120 can also have a length greater than one inch. In one embodiment, stripped end length 120 does not interfere with radiolucent characteristics of electrode 100, e.g., a medical diagnosis may be ascertained with stripped end length 120 being at least partially visible in an X-Ray image of a subject.

In one embodiment, at least a portion of stripped end length 120 is coupled with the bottom surface of conductive element 110 that is configured to face toward a subject wearing electrode 100. For example, a pressure sensitive adhesive on the bottom surface of the protruding portion of conductive element 110 or backing pad 105 can couple to at least a portion of leadwire 115 or stripped end length 120 with electrode 100. Stripped end length 120 can also attach to other portions of the bottom surface of conductive element 110. In one embodiment, the coupling between stripped end length 120 and the bottom surface of conductive element 110 is sufficient for current to follow a path between leadwire 115 and conductive element 110 via stripped end length 120. In one embodiment, the coupling between stripped end length 120 and the bottom surface of conductive element 110 is achieved with a conductive or non-conductive pressure sensitive adhesive, and in the absence of rivets, grommets and washers.

The individual extensions of stripped end length 120 can have various cross sectional shapes. For example, the extensions may have a substantially round cross section. In one embodiment, at least one extension of stripped end length 120 is substantially flat. For example, a flattened extension may have at least two flat surfaces, such as a top surface (e.g., contacting and substantially flush with the bottom surface of conductive element 110) and a bottom surface (e.g., configured to face toward a subject wearing electrode 100 and substantially flush with at least one component of electrode 100 such as at least one bonding layer 130). These two surfaces can be substantially parallel. In one embodiment, at least one extension of stripped end length 120 has substantially quadrilateral, rectangular, or square cross sections. In one embodiment, stripped end length 120 and leadwire 115 are radiolucent.

Electrode 100 may include at least one hotmelt adhesive 125. In one embodiment, hotmelt adhesive 125 is disposed about leadwire 115 to for example, fill a gap between leadwire 115 and the other components or layers of electrode 100. Hotmelt adhesive 125 may also secure leadwire 115 to electrode 100 preventing displacement of leadwire 115 when leadwire 115 is under stress or tension due to pulling or other strain forces. Hotmelt adhesive 125 may be a flexible adhesive.

Electrode 100 can include at least one bonding layer 130. In one embodiment, bonding layer 130 includes a low elongation, high tensile strength film, such as 0.0005 inch thick polyester. The top surface and the bottom surface of bonding layer 130 may include an adhesive to couple bonding layer 130 with proximate electrode 100 components, (e.g., conductive element 110, leadwire 115, or insulator 135). The adhesive can be conductive or non-conductive, pressure sensitive, epoxy, or cyanoacrylate. In one embodiment, the adhesive on the top surface of bonding layer 130 couples bonding layer 130 with stripped end length 120, holding stripped end length 120 in place between the top surface of bonding layer 130 and the bottom surface of conductive element 110. In one embodiment, adhesive couples stripped end length 120 with the top surface of bonding layer 130 and the bottom surface of conductive element 110. In one embodiment, portions of hotmelt adhesive 125 contact stripped end length 120, conductive element 110, or bonding layer 130. Bonding layer 130 can also cover a portion of leadwire 115. The bonding layer 130 may overlap stripped end length 120 by at least $\frac{1}{8}^{th}$ of an inch.

In one embodiment, electrode 100 includes at least one insulator 135. Insulator 135 may include a non-conductive layer of flexible, stretchable film, such as polyethylene foam. While the thickness of insulator 135 may vary, in one embodiment, insulator is $\frac{1}{32}^{nd}$ of an inch thick. The top surface or the bottom surface of insulator 135 may include an adhesive, such as a pressure sensitive adhesive. Insulator 135 can insulate the subject from current that may be present at stripped end length 120. In one embodiment, insulator 135 is disposed between the subject and stripped end length 120 so that the subject does not directly contact stripped end length 120. Insulator 135 may overlap stripped end length 120 by at least $\frac{1}{8}^{th}$ of an inch.

In one embodiment, at least a portion of the bottom surface of insulator 135 contacts the subject. The top surface of insulator 135 may contact portions of at least one of bonding layer 130, conductive element 110, and backing pad 105. The top surface of insulator 135 may also contact portions of hotmelt adhesive 125, leadwire 115, or stripped end length 120. Bonding element 130 may be included as part of insulator 135, or they may be distinct elements. The outer boundary of insulator 135 may follow a portion of the footprint of electrode 100 delineated by backing pad 105, without extending beyond this footprint. In one embodiment, the surface area of insulator 135 (top or bottom surface) is less than one third the surface area of backing pad 105 (top or bottom surface).

Electrode 100 can also include at least one conductive gel layer 140. Conductive gel layer 140 generally provides an interface between conductive element 110 and the subject's skin to deliver current to, and receive signals from the subject's body. In one embodiment, conductive gel layer 140 is a conductive gel pad. The outer surfaces of conductive gel layer 140 can include an adhesive to couple with proximate electrode 100 components (e.g., insulator 135, or conductive element 110). The bottom outer surface of conductive gel layer 140 can couple with the subject wearing electrode 100. Conductive gel layer 140 may include a conductive adhesive polymer hydrogel, gel pad, gel sponge, or conductive fluid. Conductive gel layer 140 may include gel disposed in a membrane. The top and bottom outer surfaces of the membrane can include adhesive. In one embodiment, conductive gel layer 140 includes conductive fluid in a membrane, and the passing of current through electrode 100 to the subject may release at least some of the conductive fluid from the membrane, for example by rupturing the membrane.

In one embodiment, conductive gel layer 140 covers the bottom surface of conductive element 110. Conductive gel layer 140 can cover more than the complete bottom surface of conductive element 110. For example, conductive gel layer 140 can extend at least ¼ inch beyond the edges (e.g. footprint) of conductive element 110. In one embodiment, conductive gel layer 140 directly contacts conductive element 110 and extends at least ⅛ inch beyond the edges of conductive element 110. Intervening elements, such as insulator 135, bonding layer 130, or stripped end length 120 may be present between the top surface of conductive gel layer 140 and the bottom surface of conductive element 110. For example, the top surface of conductive gel layer 140 can couple with at least one of the bottom surface of insulator 135, the bottom surface of bonding layer 130, the bottom surface of hotmelt layer 125, stripped end length 120, leadwire 115, the bottom surface of conductive element 110, and the bottom surface of backing pad 105. In one embodiment, conductive gel layer 140 has a similar shape but different size than electrode 100.

For example, electrode 100 may have a circular shape and include a circular conductive gel layer 140, or a rectangular shape and a rectangular conductive gel layer 140.

In one embodiment, at least a portion of stripped end length 120 is disposed between the bottom surface of conductive element 110 and the top surface of conductive gel layer 140. Conductive gel layer 140 may have at least one of an area of at least 12.6 in$^2$, or a diameter of substantially 4 inches (e.g., 3.5 to 4.5 inches). In some embodiments, conductive gel layer 140 has an area of at least 6.5 in$^2$, or a diameter of substantially 3 inches (e.g., 2.5 to 3.5 inches), or an area of at least 4.0 in$^2$, or a diameter of substantially 2.25 inches (e.g., 2.0 to 3.0 inches). In one embodiment, conductive gel layer 140 is rectangular shaped with a length of substantially 5 inches (e.g., 4.5 to 5.5 inches) and a width of substantially 3.5 inches (e.g. 3.0 to 4.0 inches). In some embodiments, conductive gel layer 140 is rectangular shaped with a length of substantially 3.75 inches (e.g., 3.25 to 4.25 inches) and a width of substantially 2.25 inches (e.g. 1.75 to 2.75 inches), or with a length of substantially 2.25 inches (e.g., 1.75 to 2.75 inches) and a width of substantially 1.75 inches (e.g. 1.25 to 2.25 inches). In one embodiment, at least part of the edge of backing pad 105 extends at least a half inch beyond the edge conductive gel layer 140. In one embodiment, conductive gel layer 140 or electrode 100 and its components are in compliance with the requirements of the ANSI or AAMI DF80 standards for electrodes. Protruding tabs or extensions that may protrude out from the edges of conductive element 110 may extend beyond the footprint of conductive gel layer 140.

Electrode 100 may also include at least one tab 145. In one embodiment, tab 145 is a plastic sheet protruding from electrode 100 that the subject or health care provider may use as a handle to remove electrode 100 from the subject or from its packaging. Tab 145 can couple to any part of electrode 100, such as the bottom surface of insulator 135, covering the area where hotmelt adhesive 125 may hold leadwire 115 in position. The bottom surface of tab 145 may contact the subject. In one embodiment, this bottom surface, and the portion of the top surface of tab 145 that protrudes out from backing pad 105 are free of adhesive. In one embodiment, tab 145 identifies itself as a tab to be used for gripping when adjusting, placing, moving, or removing electrode 100. For example, tab 145 may include written instructions, symbols, or may be brightly colored (e.g. red) to indicate that it may operate as a handle or grab tab. In one embodiment, tab 145 is square shaped having dimensions of 1.25×1.25 inches.

In one embodiment, electrode 100 includes at least one label 150. Labels 150 can be disposed on the top side of backing pad 105, or can protrude from electrode 100. In one embodiment, labels 150 include printed instructions (e.g, words, pictures, or symbols) for the operation, placement, or removal of electrode 100 from the subject. Labels 150 may be made from a flexible printable film and coupled to electrode 100 with a pressure sensitive adhesive. Labels 150 can have a similar shape as electrode 100 (e.g., circular, rectangular) and can be smaller than backing pad 105. Labels 150 can be separate elements attached to electrode 100, or can be printed directly on electrode components, such as the top surface of backing pad 105.

Figure 5A:
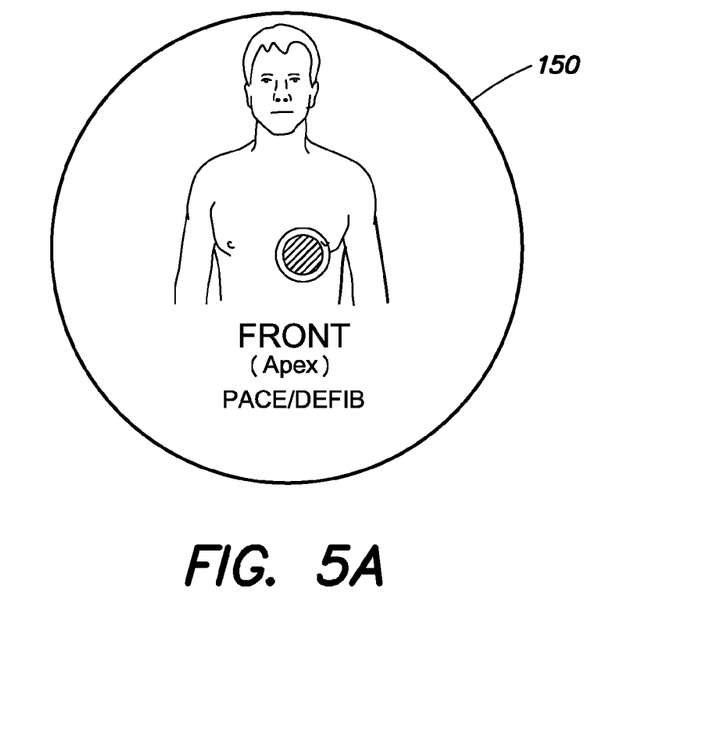
FIG. 5A is a plan view of a top surface of an electrode label that may be used with the embodiment of FIGS. 1 and 2 in accordance with an embodiment.
Figure 5B:
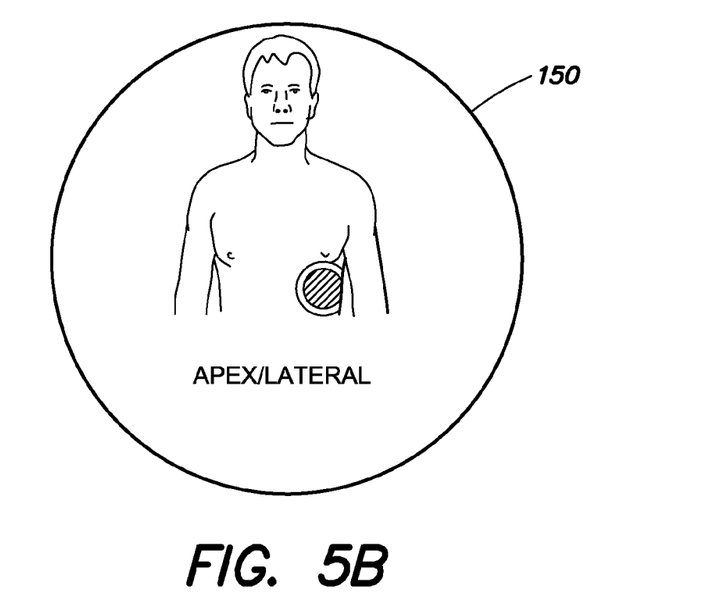
FIG. 5B is a plan view of a top surface of an electrode label that may be used with the embodiment of FIGS. 1 and 2 in accordance with another embodiment.
Figure 6A:
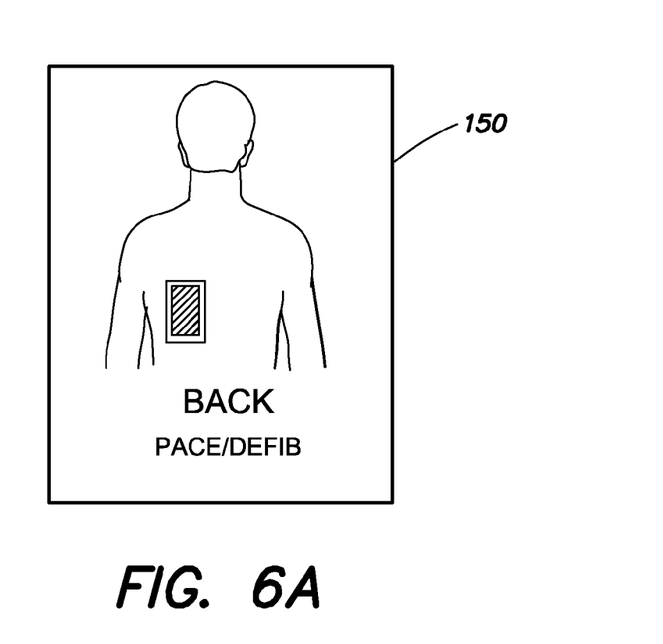
FIG. 6A is a plan view of a top surface of an electrode label that may be used with the embodiment of FIGS. 3 and 4 in accordance with an embodiment.
Figure 6B:
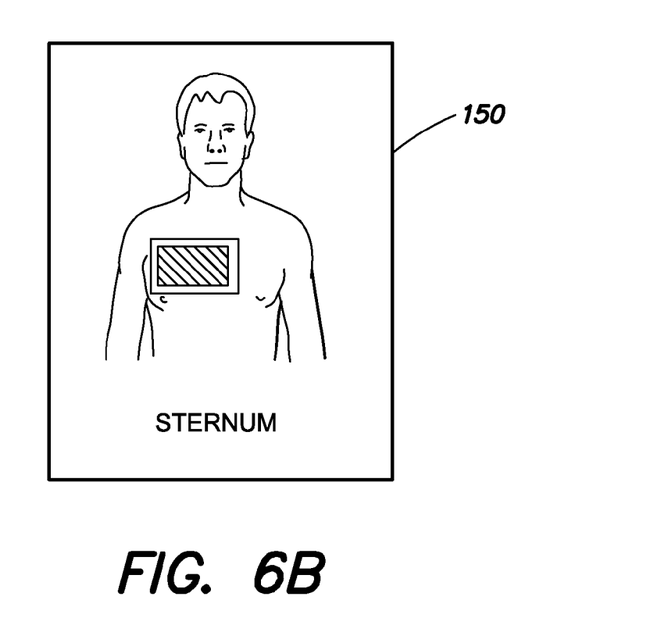
FIG. 6B is a plan view of a top surface of an electrode label that may be used with the embodiment of FIGS. 3 and 4 in accordance with an embodiment.

FIG. 5A depicts an example label 150 with instructions printed on the label to direct a user (e.g., the subject or a health care technician) to place electrode 100 in an anterior position on the subject's chest proximate to the subject's heart. FIG. 5B depicts an example label 150 indicating that electrode 100 is to be placed in a lateral position on the subject. FIG. 6A depicts an example label 150 with instructions printed on the label to direct a user to place electrode 100 in a posterior position on the subject's back proximate to the subject's heart. FIG. 6B depicts an example label 150 indicating that electrode 100 is to be placed in an anterior position on the subject.

In one embodiment, electrode 100 includes the following components in this order from top to bottom: label 150, backing pad 105, conductive element 110, stripped end length 120 of leadwire 115, hotmelt adhesive 125, bonding layer 130, insulator 135, conductive gel layer 140, and tab 145. Other configurations are possible. For example, insulating layer 135 can include bonding layer 130, tab 145, or labels 150 that can be absent or separate from electrode 100. Further at least some hotmelt adhesive 125 can surround leadwire 115 so that some hotmelt adhesive 125 can be present on top and bottom surfaces of leadwire 115.

Electrode components in this example may adhere to adjacent components by use of adhesive on their surfaces, and one surface of one element can adhere to more than one adjacent component. For example, the bottom surface of backing pad 105 can contact the top surfaces of conductive element 110, bonding layer 130, insulator 135, and conductive gel 140. The subject wearing electrode 100 can also contact these and other components. The surfaces of electrode components may, but need not, cover the entire surfaces of their adjacent components. For example, conductive gel layer 140 can cover the entire bottom surface of conductive element 110 with intervening stripped end length 120 being present between conductive gel layer 140 and conductive element 110. In one embodiment, with intervening stripped end length 120 or leadwire 115 present between these two layers (140 and 110), conductive gel layer 140 can cover the entire bottom surface of conductive element 110.

In one embodiment, electrode components being disposed on, proximate to, coupled with, connected to, attached to, or located between any electrode component includes the components being at least partially disposed on, proximate to, coupled with, connected to, attached to, or located between any electrode component. Intervening components may be present.

Figure 7:
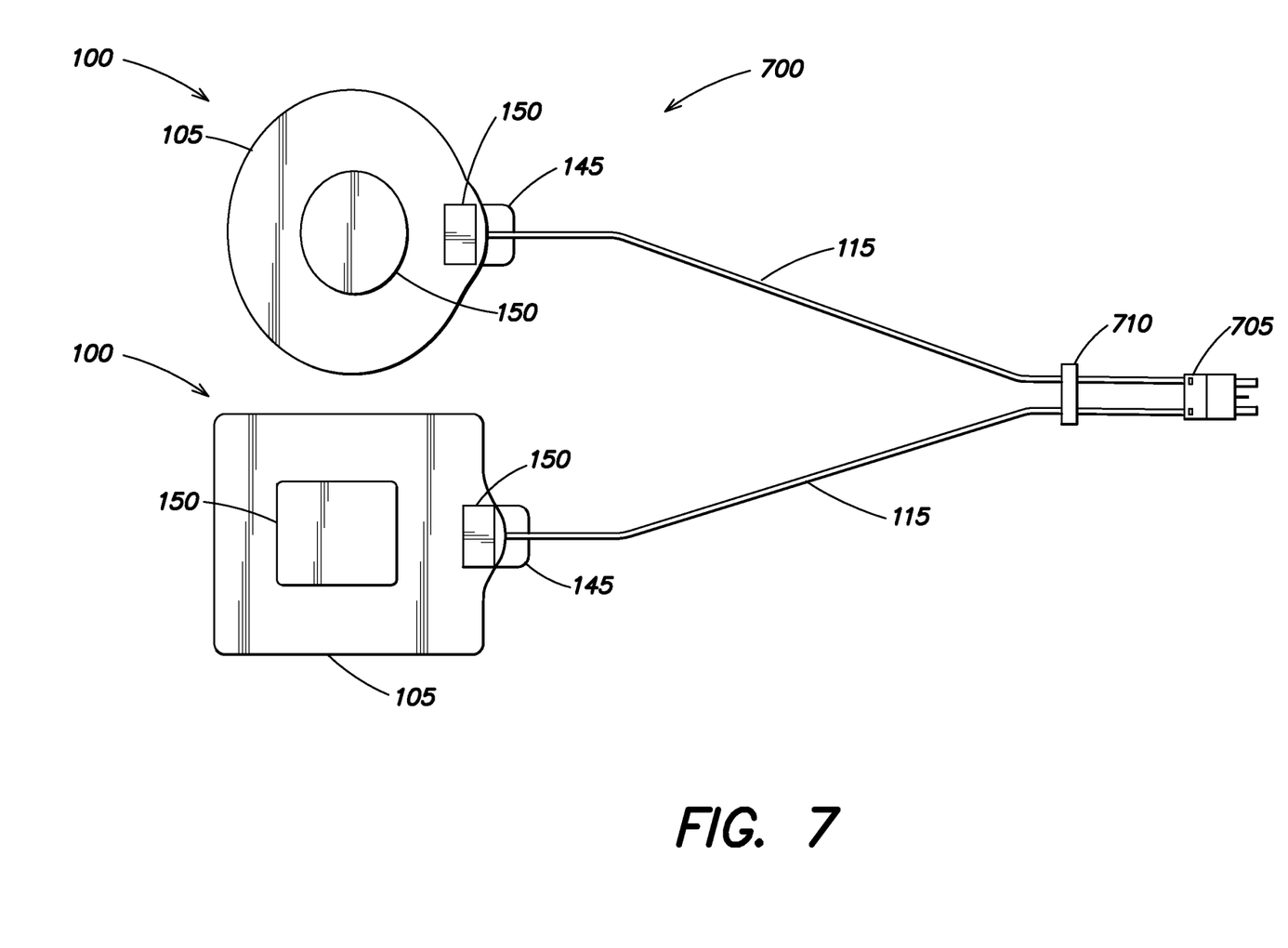
FIG. 7 is a plan view depicting a pair of electrodes as part of a biomedical electrode system in accordance with an embodiment.

FIG. 7 is a plan view of an electrode system 700 that includes a pair of electrodes 100. In one embodiment, a plurality of electrodes 100 are part of biomedical electrode system 700 that is configured to treat or monitor a subject. For example, the subject can wear two electrodes 100. Leadwires 115 run from each electrode to a defibrillating, pacing, monitoring, or control unit (not shown in FIG. 7), which may include a power source, to control the operation of electrodes 100 or to process information (e.g., EKG, EEG) detected by electrodes 100. The two electrodes 100, leadwires 115, and the subject's body form part of a circuit so that electrical energy or signals may be passed to or from the subject via a plurality of electrodes 100. The control unit, power supply or other devices can also be included in this circuit.

Electrodes 100 may have different shapes for placement on different areas of the subject's body, e.g., anterior, posterior, or lateral. With reference to FIG. 7, one electrode 100 may be substantially circular for anterior placement on the subject's chest, for example proximate to the subject's heart. Another electrode 100 may be substantially rectangular for posterior placement on the subject's back, for example also proximate to the subject's heart. Electrodes 100 may defibrillate, pace, or monitor the heart.

In one embodiment, at least one connector 705 receives at least one leadwire 115. For example, a first end of connector 705 can receive a terminal end of leadwire 115 that is distal from stripped end length 120. A second end of connector 705 can interface with at least one defibrillator, power supply, monitor, pacing unit, or control system. Connector 705 can secure leadwires 115, providing strain relief. In one embodiment, leadwires 115 are connected to connector 705 by a press fit, or anchored by cold-forming dimples in connector 705. Connector 705 may be made of a substantially rigid plastic or other material. In one embodiment, connector 705 receives a first leadwire 115 that is coupled with a substantially circular electrode 100, and connector 705 receives a second leadwire 115 that is coupled with a substantially rectangular electrode 100. An indication of which leadwire 115 couples with which electrode 100 can be printed on leadwire 115 or on a label attached to leadwire 115, for example near the point of connection with connector 705.

In one embodiment, biomedical electrode system 700 includes at least one containment element 710. At least one leadwire 115 can pass through containment element 710 between connector 705 and electrode 100. For example, containment element 710 may be located within three inches, measuring along the length of leadwire 115, from connector 705. Containment element 710 can secure leadwires 115, maintain the integrity of the connection between leadwires 115 and connector 705, and provide strain relief. Containment element 710 can be made of a substantially rigid plastic or other material. In one embodiment, containment element 710 is an integral unit with one through-hole for each leadwire 115. Containment element 710 can have a variety of shapes, for example, rectangular, square, cubed, spherical, or elongated and curved, having a profile similar to a football.

Figure 8:
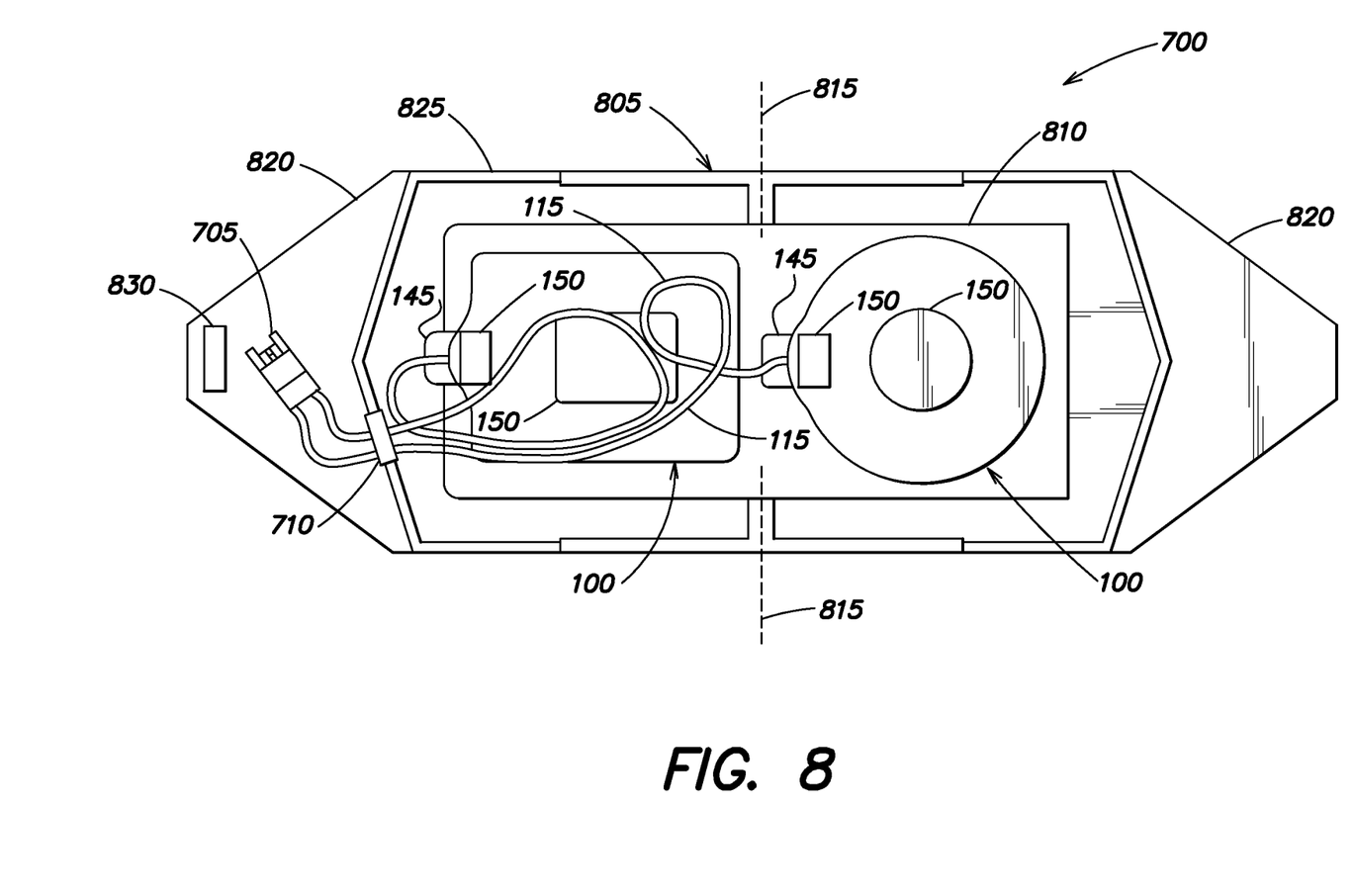
FIG. 8 is a plan view depicting a pair of electrodes as part of a biomedical electrode system in accordance with an embodiment.

FIG. 8 is a plan view depicting biomedical electrode system 700. In one embodiment, electrode system 700 is included in package 805, such as a book or pouch. Package 805 can be made of plastic, and can contain at least two electrodes 100 that have been assembled and are ready to be positioned on a subject. In one embodiment, package 805 has sleeves, with one or more electrode 100 disposed in each sleeve. Package 805 may also include layer 810, such as a polyester film. The adhesive bottom surfaces of electrode components can attach to a coated surface of layer 810 when disposed in package 805. In one embodiment, package 805 and layer 810 can fold, substantially in half along axis 815. Flaps 820 can close over package 805 when package 805 is in a folded configuration.

Edges 825 can assist in the closing of package 805 and maintain the integrity of package 805 in a closed position. Edges 825 can be reinforced. In one embodiment, containment element 710 is located at edges 825 with leadwires 115 passing through containment element 710. In one embodiment, containment element 710 seals leadwires 115 to package 805. This seal can be airtight. Connector 705 can be located in the part of package 805 that includes flap 820, which may include a separate pouch for connector 705, segregating connector 705 from the other components of electrode 100 and biomedical electrode system 700. This can prevent sharp or hard parts of connector 705 from damaging other components. The leads of connector 705 can be secured in element 830 to secure connector 705 and other electrode system components. Electrodes 100 or biomedical electrode system 700 can be packaged in packages having different configurations than that of package 805. For example, a package can include a single bag, pouch, sleeve, or pocket for all system 700 components.

Figure 9:
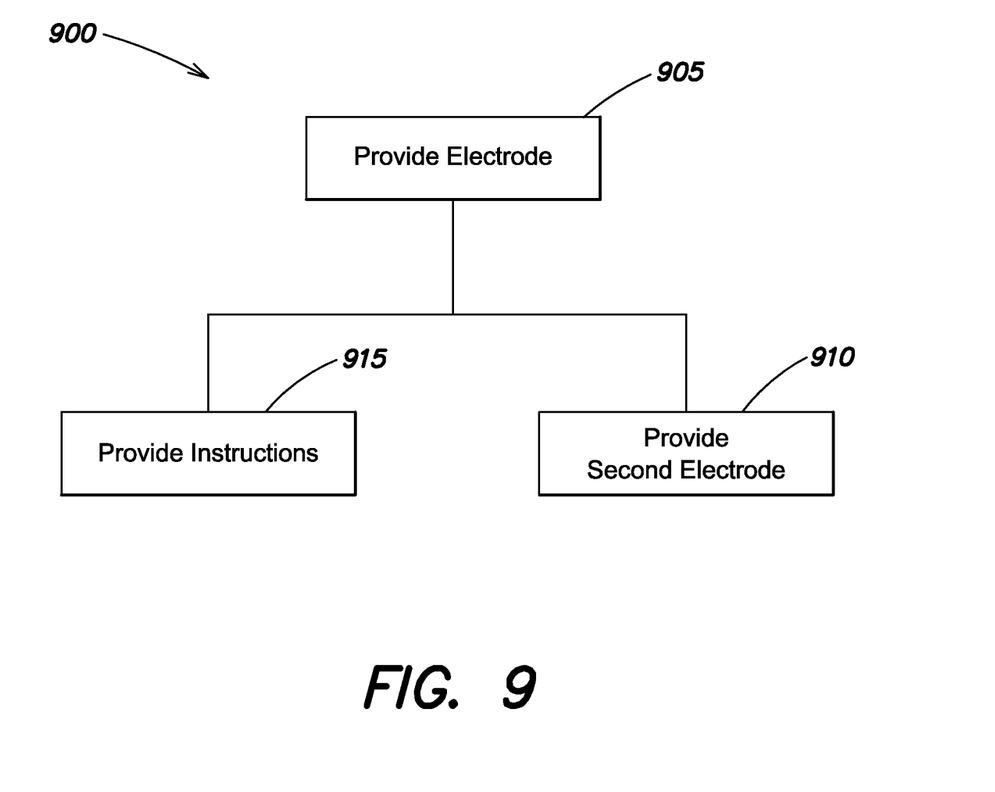
FIG. 9 is a flow chart depicting a method of facilitating care of a subject in accordance with an embodiment.

FIG. 9 is a flow chart depicting a method 900 of facilitating care of a subject. In one embodiment, method 900 includes an act of providing at least one electrode (ACT 905), such as electrode 100. For example, providing an electrode (ACT 905) may include providing an electrode having a backing pad and a conductive element attached to the bottom surface of the backing pad. The provided electrode may also include a conductive gel layer that covers at least part of a bottom surface of the conductive element. The electrode may be provided (ACT 905) with a leadwire that includes a stripped end length. At least a portion of the stripped end length can be disposed between the conductive element and the conductive gel layer.

In one embodiment, providing the electrode (ACT 905) includes providing an electrode that includes an insulator. At least part of the insulator can be disposed between the conductive gel layer and the stripped end length of the leadwire. Providing the electrode (ACT 905) may include providing the electrode with a bonding layer disposed between the insulator and the portion of the stripped end length of the leadwire. Providing the electrode (ACT 905) may also include providing at least one electrode in a package.

Method 900 may also include the act of providing a second electrode (ACT 910). For example, providing the electrode (ACT 905) may include providing an electrode configured to be placed on the subject's body at a first location (e.g., chest) and providing a second electrode (ACT 910) may include providing an electrode configured to be placed on the subject at a second location (e.g., back). The electrode and the second electrode may have different sizes, shapes or characteristics tailored to different parts of the subject's body.

In one embodiment, method 900 includes an act of providing instructions to operate the electrode (ACT 915). The instructions can be provided on at least one label attached to or printed on the electrode or its packaging. The instructions can also be provided (ACT 915) on a sheet or label separate from the label and located, for example, in the packaging. The instructions may be provided (ACT 915) using words, symbols, images, and combinations thereof. In one embodiment, providing instructions (ACT 915) includes providing instructions directing a user (e.g., the subject, a health care provider, or an assistant) to position at least one electrode on the subject, for example on the subject's chest or back, proximate to the heart. Instructions can also be provided (ACT 915) to position electrodes on the subject's anterior (e.g., front, chest) or posterior (e.g., back), as well as other areas of the subjects body. In one embodiment, providing instructions (ACT 915) includes providing instructions to adhere the electrode to the subject, proximate to the subject's heart. In one embodiment, providing instructions (ACT 915) includes providing instructions to remove the electrode from the subject.

Having now described some illustrative embodiments, it is apparent that the foregoing is illustrative and not limiting, having been presented by way of example. In particular, although many of the examples presented herein involve specific combinations of method acts or system elements, those acts and those elements may be combined in other ways. Acts, elements and features discussed only in connection with one embodiment are not intended to be excluded from a similar role in other embodiments.

Note that in FIGS. 1 through 9, the enumerated items are shown as individual elements. In actual implementations of the systems and methods described herein, however, they may be part of or inseparable components of other elements.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations. References to any act or element being based on any information, act or element may include embodiments where the act or element is based at least in part on any information, act, or element.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment, inclusively or exclusively, in any manner consistent with the aspects and embodiments disclosed herein.

References to "or" may be construed as inclusive so that any terms described using "or" may indicate any of a single, more than one, and all of the described terms. Embodiments, acts, or elements are not essential unless recited as such.

One skilled in the art will realize the systems and methods described herein may be embodied in other specific forms without departing from the characteristics thereof. For example, electrode components may have shapes other than circular and rectangular. Electrode components can be circular, elliptical, quadrilateral, square, or other designs, and can have different sizes for larger (e.g. adult or obese) or smaller (child, pediatric, or neonatal) subjects. Electrodes configured for placement on a particular part of the subject's anatomy (e.g., chest, back, legs, head) can be ergonomically configured to adhere to that anatomical feature. A plurality of electrodes can be placed on one region of the subject, e.g., two electrodes can be placed on the subject's chest, back, or lateral portion, with at least one other electrode placed at another location on the subject. Electrodes can be concave or convex. Electrodes can have more fanciful or arbitrary shapes or patterns (e.g, star, unicorn, smiley face, dinosaur, football, baseball, soccer ball, basketball, celebrity, athletic, or cartoon figure) to for example ease the mental anguish of a child with a medical condition who wears the electrode. Further, the adhesive couplings described herein can be permanent or reversible. For example, they can be peeled apart for maintenance or replacement purposes. Other couplings, press fit, mechanical, fasteners, etc can also couple elements together. The couplings can allow electrical currents to pass between the subject and leadwire 115 via a plurality of components (e.g., stripped end length 120, conductive element 110, and conductive gel layer 140) directly or via intervening components. Further, electrode components depicted in phantom are part of the electrode and merely may not be entirely visible from the perspective of the associated drawings.

The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An electrode comprising:
   a backing pad having a top surface and a bottom surface;
   a conductive element attached to the bottom surface of the backing pad;
   a conductive gel layer covering at least part of a bottom surface of the conductive element;
   a bonding layer disposed at least in part between the conductive element and the conductive gel layer and adhesively coupled between the conductive element and the conductive gel layer;
   a leadwire having a stripped end length, at least a portion of the stripped end length disposed between the conductive element and at least one of the bonding layer and the conductive gel layer and adhesively and electrically coupled to the conductive element and adhesively coupled to the bonding layer; and
   an insulator including an adhesive disposed on a lower surface thereof, the insulator and the adhesive each distinct from the bonding layer, the insulator disposed on the conductive gel layer between a portion of the conductive gel layer and the portion of the stripped end length of the leadwire.

2. The electrode of claim 1, wherein a bottom surface of the insulator and the bottom surface of the backing pad include adhesive, and wherein a surface area of the bottom surface of the insulator is less than half of a surface area of the bottom surface of the backing pad.

3. The electrode of claim 1, wherein the bonding layer is disposed at least in part between the insulator and the portion of the stripped end length of the leadwire.

4. The electrode of claim 1, further comprising:
   a hotmelt adhesive disposed on the leadwire.

5. The electrode of claim 1, further comprising:
   a label on the top surface of the backing pad, the label including instructions associated with the electrode.

6. The electrode of claim 1, further comprising:
   a tab extending from the backing pad, a surface of the tab being free of adhesive.

7. The electrode of claim 1, wherein the leadwire includes a conductive carbon element, and wherein the stripped end length includes a plurality of stripped extensions.

8. The electrode of claim 7, wherein the plurality of stripped extensions are in a fanned configuration, and wherein at least one of the plurality of stripped extensions has a round cross section.

9. The electrode of claim 7, wherein the conductive carbon element includes at least one metal strand woven with at least one carbon strand.

10. The electrode of claim 1, wherein the portion of the stripped end length of the leadwire is disposed proximate to a bottom surface of the conductive element.

11. The electrode of claim 1, wherein the electrode is radiolucent.

12. The electrode of claim 1, wherein the electrode includes at least one of a therapy electrode, a treatment electrode, a stimulating electrode, and a monitoring electrode, and wherein the electrode is configured to adhere to a subject.

13. The electrode of claim 1, wherein the insulator includes a non-conductive layer of film disposed between the portion of the conductive gel layer and a bottom side of the portion of the stripped end length of the leadwire.

14. The electrode of claim 1, wherein the conductive element includes a protrusion including writing or symbols indicating information about one of the electrode and the conductive element.

15. The electrode of claim 1, wherein the conductive gel layer includes gel disposed in a membrane.

16. The electrode of claim 1, further comprising a tab coupled to a lower surface of the conductive gel layer and protruding from the electrode.

17. A biomedical electrode system, comprising:
   a first electrode configured to adhere to a first location of a subject; and
   a second electrode configured to adhere to a second location of the subject;
   the first electrode including:
   a backing pad having a top surface and a bottom surface;

a conductive element attached to the bottom surface of the backing pad;

a conductive gel layer covering at least part of a bottom surface of the conductive element;

a bonding layer disposed at least in part between the conductive element and the conductive gel layer and adhesively coupled between the conductive element and the conductive gel layer;

a leadwire having a stripped end length, at least a portion of the stripped end length disposed between and adhesively and electrically coupled to the conductive element and adhesively coupled to the bonding layer; and an insulator including an adhesive disposed on a lower surface thereof, the insulator and the adhesive each distinct from the bonding layer, the insulator disposed on the conductive gel layer between at least a portion of the conductive gel layer and the portion of the stripped end length of the leadwire.

18. The system of claim 17, wherein the first electrode is an anterior electrode configured for placement proximate to a chest of a subject, and wherein the second electrode is a posterior electrode configured for placement proximate to a back of the subject.

19. The system of claim 18, wherein the first electrode and the second electrode are configured to form part of a circuit to apply electrical energy to a subject.

20. The system of claim 18, wherein the anterior electrode has a substantially circular profile, and wherein the posterior electrode has a substantially rectangular profile.

21. The system of claim 17, further comprising:

a connector configured to receive the leadwire of the first electrode and to receive a leadwire of the second electrode.

22. The system of claim 21, further comprising:

a containment element configured to secure the leadwire of the first electrode and the leadwire of the second electrode.

23. The system of claim 17, wherein the first electrode is an anterior electrode configured for placement proximate to a chest of a subject, and wherein the second electrode is an anterior electrode configured for placement proximate to the chest of the subject.

* * * * *